US012790467B2

(12) United States Patent
Haas

(10) Patent No.: US 12,790,467 B2
(45) Date of Patent: Nov. 10, 2026

(54) CONTACT MEDIUM

(71) Applicant: ECCO SPRAY LTD., Dublin (IE)

(72) Inventor: Helmut Haas, Heppenheim (DE)

(73) Assignee: ECCO SPRAY LTD., Dublin (IE)

( * ) Notice: Subject to any disclaimer, the term of this patent is extended or adjusted under 35 U.S.C. 154(b) by 676 days.

(21) Appl. No.: 18/251,304

(22) PCT Filed: Nov. 4, 2020

(86) PCT No.: PCT/EP2020/080993
§ 371 (c)(1),
(2) Date: May 1, 2023

(87) PCT Pub. No.: WO2022/096089
PCT Pub. Date: May 12, 2022

(65) Prior Publication Data

US 2023/0407056 A1 Dec. 21, 2023
US 2024/0343891 A9 Oct. 17, 2024

(51) Int. Cl.

| | |
|---|---|
| ***C08L 1/28*** | (2006.01) |
| ***A61B 8/00*** | (2006.01) |
| ***C08J 3/075*** | (2006.01) |
| ***C08K 5/05*** | (2006.01) |
| ***C08K 5/092*** | (2006.01) |
| ***C08K 5/098*** | (2006.01) |
| ***C08K 5/103*** | (2006.01) |

(52) U.S. Cl.
CPC ............ *C08L 1/284* (2013.01); *A61B 8/4281* (2013.01); *C08J 3/075* (2013.01); *C08K 5/05* (2013.01); *C08K 5/092* (2013.01); *C08K 5/098* (2013.01); *C08K 5/103* (2013.01); *C08J 2301/26* (2013.01); *C08J 2491/00* (2013.01); *C08K 2201/014* (2013.01); *C08L 2207/32* (2013.01)

(58) Field of Classification Search
CPC ...... C08L 1/24; C08L 2207/32; A61B 8/4281; C08J 3/075; C08J 2301/26; C08J 2491/00; C08K 5/05; C08K 5/092; C08K 5/098; C08K 5/103; C08K 2201/014
See application file for complete search history.

(56) References Cited

U.S. PATENT DOCUMENTS

| | | | | |
|---|---|---|---|---|
| 6,410,005 B1 * | 6/2002 | Galleguillos | ......... | C08F 265/04 424/47 |
| 2009/0253666 A1 * | 10/2009 | Lintner | ................ | A61K 8/9728 514/173 |
| 2013/0116331 A1 | 5/2013 | Heinar | | |
| 2014/0200450 A1 * | 7/2014 | Ragg | ........................ | A61B 8/48 424/9.5 |
| 2018/0055481 A1 | 3/2018 | Kusunoki | | |
| 2020/0253825 A1 * | 8/2020 | Peguero | .............. | A47J 36/2483 |

FOREIGN PATENT DOCUMENTS

| | | | | |
|---|---|---|---|---|
| CN | 105999312 A | 10/2016 | | |
| CN | 106692997 A | 5/2017 | | |
| DE | 4434626 C2 | 4/1996 | | |
| EP | 2415487 A1 | 2/2012 | | |
| JP | 2004503626 A | 2/2004 | | |
| JP | 2013535251 A | 9/2013 | | |
| JP | 2017153871 A | 9/2017 | | |
| WO | WO-2008134633 A1 * | 11/2008 | ........... | A61B 8/4281 |
| WO | 2009009064 A1 | 1/2009 | | |
| WO | 2012009794 A1 | 1/2012 | | |
| WO | 2016185811 A1 | 11/2016 | | |
| WO | WO-2019147940 A1 * | 8/2019 | ........... | A61B 8/4236 |
| WO | 2020196652 A1 | 10/2020 | | |

OTHER PUBLICATIONS

International Search Report for International Patent Application No. PCT/EP2020/080993 dated Aug. 5, 2021; priority document.

* cited by examiner

*Primary Examiner* — Robert S Jones, Jr.
*Assistant Examiner* — Elizabeth Amato
(74) *Attorney, Agent, or Firm* — Greer, Burns & Crain, Ltd.

(57) ABSTRACT

A contact medium for use in medical and non-medical sonography, in electrocardiography, in electroencephalography, or in defibrillation, which contains 0.05 to 2.5 wt. % of a gel-forming agent, 0.05 to 3.5 wt. % of a detergent, and 0.1 to 4.0 wt. % of an emulsifier and optionally additives as well as water as the remaining element.

16 Claims, No Drawings

CONTACT MEDIUM

RELATED APPLICATIONS

This application is a national phase of International Application No. PCT/EP2020/080993 filed on Nov. 4, 2020, the entire disclosure of which is incorporated herein.

FIELD AND BACKGROUND OF THE INVENTION

The present invention relates to a contact medium, which is preferably used in medical sonography. However, the contact medium according to the invention can also be used in non-medical methods for the examination of technical structures by means of ultrasonics as well as in other medical procedures which are not based on ultrasonics but require a contact medium.

Sonography, also known as echography or ultrasonic examination, is an imaging procedure for non-destructive investigation of organic or technical structures, which is based on the fact that coupled sound waves in different media propagate at different speeds and are partially reflected at interfaces with different wave impedances. The wave impedance refers to a resistance that opposes the propagation of the waves. As the difference in the wave impedance at an interface increases, the reflected portion of the coupled waves also increases. The time-of-flight and strength of the reflected waves are detected and translated into structural information.

A significant advantage of sonography in medical imaging diagnostics compared to, for example, X-ray examinations, e.g., in computed tomography (CT), lies in the harmlessness of the sonic waves used. Instrument-related expenditures and associated costs as well as spatial requirements are also generally significantly less in sonography than in the case of computed tomography or, for example, magnetic resonance imaging, for which reason sonographic diagnostics is also used in smaller medical practices where it can be used to provide sufficiently meaningful information.

In medical sonography for the examination of organic structures, such as tissue, organs, blood vessels, and bones, but also for the visualization of blood flow speeds, e.g., by means of Doppler methods, ultrasonic waves in the frequency range of approximately 1-40 MHz are used. The ultrasonic waves are generated in a probe and are typically introduced into the body as short, directed sonic wave impulses via a surface. The reflected waves are received from a detector, which is also typically arranged in the probe, converted into electronic signals, and processed. Information about the examined structures is determined from the time-of-flight and the strength of the reflected waves.

In addition to examinations in which a probe is inserted into the vascular system, e.g., in body openings (vaginally, rectally) or by means of a catheter, the sonic wave impulses are introduced into the body from the outside in most applications of sonography. Here, the probe head is usually placed manually on the patient's skin by the examining physician, moved over it, and inclined at various angular positions.

Because the difference in wave impedance between air and water or organic structures, including the skin, is very large (air: approximately 410 $kg/m^2$ s; skin, fat, water, muscle: >$10^6$ $kg/m^2$ s), the ultrasonic probe must be coupled to the skin via an aqueous contact medium so that the sound is not already reflected by air pockets between the probe head and the skin surface, which are present due to unevenness and shedding on the skin.

The same applies to other examination methods in which air pockets can interfere with a measurement, such as in material testing by means of ultrasonics on non-organic, technical structures, or also in examination methods that measure very low electrical currents, such as ECG and EEG tests, in which air inclusions would greatly distort or make impossible a measurement due to the very high electrical resistance.

Medical sonography uses predominantly viscous, water-based gels produced according to different formulas as the contact medium for coupling the probe head to the skin surface. Such gels can be costly to manufacture due to their ingredients, and they have other disadvantages, as well. Due to the viscosity, for example, more gel is generally applied than needed. Thus, gel consumption is high, associated with high costs. Viscous gels often soil garments on patients who are not fully undressed, and wiping the gel consumes a large amount of paper, which requires additional costs to be incurred and must also be discarded. Often, the contact medium is perceived as unpleasantly cold by the patient. The possibility of pre-heating the contact medium on the skin of the patient prior to application is therefore desirable. However, in conventional viscous gels, this can lead to a change in physical properties, which are associated with uncontrolled drainage and film breakage. The application of the viscous gels is usually done from soft-walled disposable plastic containers that allow the gel to be pushed out. After use, these disposable containers are usually discarded, wherein significant quantities of gel remaining in the container are often discarded unused. In the application of the gel from the opening of the container, there is also always the risk that the skin of the patient will be touched, with the consequence of the germ transmission between patients.

Because the probe head must be moved on the skin during sonography, a good gliding ability is also required in addition to a good film formation with complete coverage of the skin area to be examined. Because viscous gels meet these requirements quite well, they are still predominantly used despite the disadvantages described above. In principle, however, only a thin contact medium film is required for a coupling between the probe head and the skin.

DE 44 34 626C2 describes a highly fluid ultrasonic contact medium that contains, in addition to water, a content of 0.5-10 vol. % detergents and 1-25 vol. % ethanol, wherein a satisfactory product was obtained only at a content of 1 vol. % detergents and 3-5 vol. % ethanol, said product being formed a permanent liquid film having good gliding properties and a sonic wave transmission corresponding to that of commercially available viscous contact medium gels. However, the contact medium was not accepted by users and manufacturers of ultrasonic devices due to the high ethanol content required for the sufficient film formation. There is a concern that the ethanol content will attack the material of the probe head if used for a long time. In addition, the evaporation of the ethanol in the application leads to an unpleasant cold feeling for the patient as well as an undesirable alcohol odor.

The problem addressed by the present invention was therefore to provide a new contact medium that overcomes or at least reduces the disadvantages of known contact media, in particular in medical sonography.

DESCRIPTION OF THE INVENTION

This problem may be solved by a contact medium containing:

| | |
|---|---|
| 0.05 to 2.5 wt. % | of a gel-forming agent |
| 0.05 to 3.5 wt. % | of a detergent |
| 0.1 to 4.0 wt. % | of an emulsifier |

optionally additives, preferably selected from preservatives, acidifiers, skincare additives, and mixtures thereof, and water as the remaining element, wherein the gel-forming agent is selected from the group consisting of hydroxyethyl cellulose, carboxycellulose, xanthan gum, guar gum, collagen, gelatin, pectins, chitin, starch, alginates, including sodium alginate, potassium alginate, and calcium alginate, and mixtures thereof, the detergent is a non-ionic surfactant or a mixture of non-ionic surfactants, the emulsifier is selected from the group consisting of glycerol mono fatty acid esters and glycerol di-fatty acid esters and mixtures thereof, wherein the remaining fatty acid is preferably derived from C7-C20-saturated fatty acid, C16-C20-monounsaturated fatty acid, and/or C18-C20-diunsaturated fatty acid, preferably from stearic acid, oleic acid, caprylic acid, capric acid, and/or linolenic acid, wherein the contact medium has a pH level in the range of 5 to 7.

The contact medium according to the invention is more fluid than conventional contact gels, thus possessing a lower viscosity, i.e. higher flowability. The viscosity, i.e. flowability, of the contact medium according to the invention can be adjusted by selecting the quantities of the ingredients used, in particular the gel-forming agent. The determination of the flowability of the contact medium according to the invention was carried out herein in accordance with ISO 2431 (DIN EN ISO 2431:2020-02) by measuring the efflux time of a measured volume of 100 ml contact medium composition using ISO efflux beaker no. 4 with a nozzle diameter of 4 mm at room temperature (25 °C) and, when applicable, at body temperature (37 °C). In a preferred embodiment, the contact medium according to the invention has an efflux time determined in this way at 25 °C in the range of 5 to 200 seconds, preferably in the range of 10 to 150 seconds, particularly preferably in the range of 10 to 100 seconds, and very particularly preferably in the range of 10 to 50 seconds.

If the viscosity of the contact medium according to the invention is too low, an insufficient film formation is achieved and there is a risk of film breakage. If the viscosity of the contact medium according to the invention is too high, the described disadvantages of viscous contact medium gels occur.

When used in medical sonography, the contact medium according to the invention forms a thin contact medium film with a good and seamless coverage of the treated skin area, despite its high fluidity i.e. low viscosity on the skin, without significant film breakage. At the same time, it ensures a good gliding ability of the probe head on the skin. The sonic wave transmission of the contact medium according to the invention is comparable to that of commercially available viscous contact medium gels, and sometimes even better depending on the composition.

In addition, the contact medium according to the invention can be removed from the skin easily and with less paper expenditure compared to commercially available contact gels due to the comparatively low quantity required.

A further particular advantage of the contact medium according to the invention is that it can be applied with an applicator suitable for highly fluid media, for example with a commercially available spray bottle. The spray bottle can be refilled and reused after the contact medium has been used up, thereby avoiding packaging waste. The application of the contact medium with a spray bottle also avoids touching of the patient's skin and thus reduces the risk of carrying germs from one patient to the next. For example, the contact medium can be refilled from large containers. Thus, unusable contact medium no longer remains in a disposable applicator, which would have to be disposed of, as is regularly the case with viscous contact medium gels that are sold and used in disposable applicators.

In addition, the contact medium according to the invention can be produced more cost-efficiently than commercially available contact medium gels due to the use of inexpensive ingredients.

The contact medium according to the invention can contain the gel-forming agent in a quantity between 0.05 to 2.5 wt. %. With higher proportions of the gel-forming agent in the range between over 0.5 to 2.5 wt. %, the contact medium can already have a viscosity approximating that of a commercially available contact gel, depending on the gel-forming agent used, wherein the contact medium can then still be applied thinly while having the advantages described above.

However, in a particularly preferred embodiment, the contact medium according to the invention contains the gel-forming agent in a quantity between 0.05 to 0.5 wt. %. Such a contact medium according to the invention is particularly highly fluid, but still has all the advantages described herein and can in particular be quite effectively applied, e.g., by means of a spray bottle. In addition, it is more cost-effective to manufacture, because less gel-forming agent are needed.

In addition to the gel-forming agent, detergent and emulsifier, the contact medium according to the invention can optionally contain further additives, such as preservatives, buffers or acidifiers, skincare additives, etc. Such additives can be used advantageously, but in such low quantities that they do not, or at least not significantly, impair the advantageous properties of the contact medium, such as flow and film-forming properties, gliding ability, and sonic wave transmission.

In one embodiment, the contact medium according to the present invention contains preservatives, preferably in a quantity between 0.05 to 1.0 wt. %, wherein the preservative is particularly preferably selected from the group consisting of sodium benzoate, potassium benzoate, sodium sorbate, potassium sorbate, and mixtures thereof. Too little preservative leads to no or too little preservative effect. Too high a proportion does not provide a substantial additional preserving effect and/or can adversely affect the physical and/or chemical properties of the contact medium. In one advantageous embodiment of the invention, the contact medium contains a mixture of about 0.3 to 0.5 wt. % sodium benzoate and about 0.1 to 0.3 wt. % potassium sorbate. The addition of the preservative improves the durability and shelf life of the contact medium according to the invention without significantly impairing the further advantageous properties.

The contact medium according to the invention has a pH level in the range of 5 to 7. This medium is thus already well-tolerated by the skin. In addition, it has been shown that a pH level in the range of 5 to 7 stabilizes the advantageous physical and chemical properties of the contact medium achieved by the combination of the gel-forming agent, detergent, and emulsifier according to the invention. In a further advantageous embodiment of the invention, the contact medium has a pH level in the range of 5 to 6.5, preferably in the range of 5 to 6, and particularly preferably in the range of 5 to 5.6. A lower pH level in the range of 5 to 6 or even≤5.6 is advantageous in many cases, because, among other things, it achieves better a preserving effect in the presence of preservatives than at higher pH levels.

Depending on the selection and quantities of gel-forming agent, detergent, and emulsifier as well as additives used, it can be necessary to lower and/or buffer pH level. Thus, in one embodiment, the contact medium according to the invention contains an inorganic or organic buffer system or acidifier for adjusting and/or buffering the pH level. A suitable acidifier according to the present invention is citric acid. Suitable buffer systems according to the present invention are sodium citrate-citric acid buffer or phosphate-citrate buffer, for example disodium phosphate-citric acid buffer. The required quantities of buffer or acidifier are low and are routinely determined by the person skilled in the art. In experiments, for example, a quantity of 2 wt. % citric acid has proven to be suitable for lowering the pH level of a composition according to the invention to 5.6.

Furthermore, the contact medium according to the invention can advantageously contain a skincare additive. Suitable skincare additives are known to the person skilled in the art from the field of cosmetics as well as from medical and non-medical skincare products. An advantageous skincare additive according to the present invention is, for example, aloe vera alone or in a mixture with other skincare additives. The quantity of skincare additive added is routinely to be selected so as to achieve a desired skincare effect without significantly impairing the advantageous properties of the contact medium according to the invention.

The substantial components of the contact medium according to the invention, which, when combined, achieve the physical and chemical properties of the contact medium that are advantageous for the applications described herein, are a gel-forming agent, detergent, and emulsifier.

A particularly suitable and preferred gel-forming agent according to the invention is hydroxyethyl cellulose, preferably 2-Hydroxyethyl cellulose (CAS #9004-62-0) with an average degree of substitution (DS) of 0.85-1.35 and/or a molar degree of substitution (MS) of 1.5-3.0. The gel-forming agent can be used alone or in a mixture with more of the aforementioned gel-forming agents. Hydroxyethyl cellulose that is particularly suitable as a gel-forming agent according to the invention is commercially available under the names Natrosol® (Ashland Inc.), Cellosize® (Dow Chemical), and Tylose® (Shin-Etsu) In the examples described below, the product Natrosol® 250 HX was used.

In a preferred embodiment of the contact medium according to the invention, more than 80 wt. %, preferably more than 90 wt. %, of the gel-forming agent is hydroxyethyl cellulose. In a further preferred embodiment of the contact medium according to the invention, the entire gel-forming agent is hydroxyethyl cellulose.

In one advantageous embodiment, the contact medium according to the invention contains 0.1 to 0.3 wt. % of a gel-forming agent. Surprisingly, it was shown that such a small quantity of gel-forming agent can be sufficient in order to obtain a contact medium with the properties and advantages described herein in combination with detergent and emulsifier according to the invention, in particular excellent film-forming properties, gliding ability, and sonic wave transmission.

The detergent is a non-ionic surfactant or a mixture of non-ionic surfactants. Being knowledgeable of the invention, the person skilled in the art is able to select suitable non-ionic surfactants. Preferably, the detergent is selected from the group consisting of polyethoxylated castor oil, poloxamers, and mixtures thereof. In a preferred embodiment of the contact medium according to the invention, more than 80 wt. %, preferably more than 90 wt. %, of the detergent is polyethoxylated castor oil. In a further preferred embodiment of the contact medium according to the present invention, the entire detergent is polyethoxylated castor oil, which is commercially available under the names Cremophor® or Kolliphor®. In the examples described below, the product Kolliphor® RH40 (synonym Cremophor® RH40; Macrogolglycerol Hydroxystearate, PEG-40 castor oil; CAS number: 61788-85-0; Merck KGaA, Darmstadt, Germany) was used.

In one advantageous embodiment, the contact medium according to the invention contains 0.075 to 0.5 wt. % of a detergent. Surprisingly, it was shown that such a low quantity of detergent can be sufficient in order to obtain a contact medium in the composition according to the invention having the properties and advantages described herein, in particular excellent film-forming properties, gliding ability and sonic wave transmission.

The emulsifier is selected from the group consisting of glycerol mono fatty acid esters and glycerol di-fatty acid esters and mixtures thereof, wherein the remaining fatty acid is preferably derived from C7-C20-saturated fatty acid, C16-C20-monounsaturated fatty acid, and/or C18-C20-di-unsaturated fatty acid, preferably from stearic acid, oleic acid, caprylic acid, capric acid, and/or linolenic acid.

In a preferred embodiment of the contact medium according to the present invention, more than 80 wt. %, preferably more than 90 wt. %, of the emulsifier is glycerol monofatty acid esters. In a further preferred embodiment of the contact medium according to the invention, the entire emulsifier is glycerol mono-fatty acid ester. Suitable commercially available emulsifiers according to the invention can be obtained under the name Imwitor®. In the examples described below, the product Imwitor® 742, a glycerol monocaprylocaprate (macrogol-6-glycerol caprylocaprate) available from IOI Oleo GmbH, Hamburg, Germany, was used.

In one advantageous embodiment, the contact medium according to the invention contains 0.2 to 0.8 wt. % of an emulsifier. Surprisingly, it was shown that such a low quantity of emulsifier can be sufficient in order to obtain a contact medium in the composition according to the invention having the properties and advantages described herein, in particular excellent film-forming properties, gliding ability and sonic wave transmission.

In a further advantageous embodiment, the contact medium according to the invention contains 0.1 to 0.3 wt. % of a gel-forming agent, 0.075 to 0.5 wt. % of a detergent, and 0.2 to 0.8 wt. % of an emulsifier.

The contact medium according to the invention develops its advantageous properties entirely on a water basis in spite of the low material use and thus the inexpensive manufacturability and its high fluidity, i.e., low viscosity compared to commercially available contact medium gels. The addition of a monovalent alkanol, in particular ethanol, as an additional ingredient is not required. The contact medium according to the invention therefore also has advantages compared to known highly fluid contact medium, which requires a proportion of 3 to 5 vol. % ethanol in order to obtain a product that is satisfactory in terms of film formation and sonic wave transmission but is not accepted by users and manufacturers of ultrasonic devices due to the ethanol content. A small proportion of ethanol is not disruptive in the contact medium according to the invention, but does not bring any further advantages; rather, it brings the known disadvantages. The contact medium according to the invention therefore expediently contains at most 1 wt. %, preferably at most 0.5 wt. %, of a monovalent alkanol, and particularly preferably no monovalent alkanol.

The advantageous properties of the contact medium according to the invention were only achieved with the combination of the ingredients of gel-forming agent, detergent, and emulsifier in the concentrations according to the invention. The chemical and physical properties of each of these constituents were generally known. What was unexpected and therefore surprising was their cooperation in the combination according to the invention and in the low concentrations according to the invention to form a contact medium with excellent properties, in particular in sonography. The effect of the ingredients in the contact medium according to the invention goes beyond a purely additive effect of the properties of the individual ingredients. This effect is shown by the results of the examples below. In fact, due to the known properties of the individual ingredients, disadvantages were rather to be expected with a combination of the ingredients. It is therefore assumed that the advantageous properties of the contact medium according to the invention are based on a synergistic effect of the ingredients, an effect which was not expected as such. Experiments in which individual ingredients were omitted or used in concentrations outside the ranges according to the invention confirm this effect.

For example, in conventional contact medium gels, the formation of a contiguous contact medium film and a good gliding ability of the sonography probe head on the skin are substantially attributed to the high concentrations of gel-forming agents. With significantly lower concentrations of gel-forming agents in order to achieve a more highly fluid or lower viscous consistency than with conventional contact medium gels, it was initially expected that the film-forming and gliding properties would be worse. In fact, at the low concentrations of gel-forming agents according to the present invention, without the two further ingredients of detergent and emulsifier, even a formation of spherical gel drops as well as foam formation was observed, which opposed the suitability as a contact medium for sonography. Although the addition of detergent according to the invention reduced the formation of the spherical gel droplets, which may have been due to a change in surface tensions, the film-forming properties were still poor. In addition, significant quantities of air bubbles (foam formation) formed, which made this combination of gel-forming agent and detergent appear unusable for use as a contact medium in sonography, because the contact medium is specifically intended to eliminate the disruptive influences of air pockets when coupling the sound waves into the skin. The addition of emulsifier alone to the gel-forming agent slightly improved the film-forming properties, but droplet and foam formation was still observed. It was only in the inventive combination of gel-forming agent, detergent, and emulsifier that a particularly good film formation and gliding properties and a significant reduction or disappearance of the disruptive gas bubbles and a good sound wave transmission were found, despite the low concentrations.

With a low material use and thus inexpensive manufacturability, the combination according to the invention resulted in a contact medium that has comparable or even better sonic wave transmission properties than commercially available contact gels and at the same time has advantages in handling and use due to its high fluidity, such as sprayability, and a complete coverage of the treated skin area without significant film breakage and good gliding ability. The advantageous properties of the contact medium according to the invention are also preserved when the contact medium is heated, at least to a temperature at which the patient feels comfortable, for example 37 °C. (body temperature). In addition, when using a contact medium sprayed from a distance, the risk of germ transmission is extremely low.

EXAMPLES

In test series, different compositions of gel-forming agent, detergent, and/or emulsifier were produced individually and in different combinations as well as at different concentrations and checked for their properties, such as film formation, wetting, durability of the contact medium film, formation of gas bubbles, sprayability from pump spray bottles, gliding properties (including probe head gliding ability on the skin), suitability as a sonography contact medium (sound wave transmission). These properties of the compositions were tested using both an "in vitro" model and an "in vivo" model on the patient.

In Vitro Model

In the in vitro model, a patient's skin was simulated by a commercially available office film wrapper with a slightly rough surface and the contact surface of a probe head by a film wrapper having a particularly smooth surface. The formation, uniformity, and durability of the contact medium film were tested on the office foil wrapper having a slightly rough surface. The uniformity of the contact media film was visually assessed, and the durability was assessed through observation over time. The gliding properties of the contact medium were also tested and comparatively assessed by rubbing the compositions with disposable PE gloves. The formation or absence of gas bubbles was visually assessed.

The sprayability was assessed by observing the spray cone exiting the nozzle upon spraying the composition from a commercially available spray bottle. With a spray cone angle of about 30°, a good sprayability was assumed, and with a spray cone angle of 50°, a very good sprayability was assumed.

In Vivo Model

In the "in vivo" model on the patient, the properties of the compositions were tested as a contact medium as in a conventional sonography. The sonic transmission properties of the contact medium were visually assessed by comparing obtained sonography images to those obtained with a commercially available contact medium gel (Sonogel, Sonogel Vertriebs GmbH) used in medical sonography. In the same patient, prominent organ structures of the same organ were imaged with different compositions of the contact medium.

The bubble-free formation of an even liquid film and the gliding ability of the probe head were also assessed in the in vivo model on the patient, as well as the carrying along of a liquid film upon exceeding the limits of the wetted region.

Preparation of Compositions

In the experiments described below, the following ingredients were used in order to prepare compositions:

a) Gel forming-agent: Hydroxyethyl cellulose (Natrosol™ 250HX)

b) Detergent: Polyethoxylated castor oil (Kolliphor® RH40, CAS #61788-85-0)

c) Emulsifier: Glycerol monocaprylocaprate (Imwitor® 742)

The gel-forming agent Natrosol is present as a powder, while the detergent Kolliphor and the emulsifier Imwitor are present as waxy masses. Imwitor is homogenized for about 12 hours in the heating chamber at 60 °C before the start of production. Kolliphor and water (distilled $H_2O$) are also preheated to 60 °C. While stirring, the Imwitor preheated to 60 °C is first stirred into the water, and then Kolliphor is added while stirring. Subsequently, the powdered Natrosol is gradually introduced at low doses while stirring strongly so as to avoid clumping. The composition is stirred until it is homogeneous and then cooled and left standing until any foam formed during production has disintegrated. The composition can then be filled and, if applicable, sterilized in an autoclave.

Additives such as preservatives, etc., can be introduced after addition of the Kolliphor and/or after stirring of the Natrosol and dissolved through stirring. The pH level can be adjusted after the addition of the Kolliphor and/or after the stirring of the Natrosol with ongoing pH level measurement by adding acid or buffer, e.g. citric acid. To achieve a pH level of about 5.5-5.6, about 1.5-2.0 wt. % of citric acid was used in a conventional composition.

Example 1

In test series, individual components (gel-forming agent, detergent, and emulsifier), combinations of two components, and combinations of all three components according to the invention were first investigated and assessed in different compositions with regard to different properties (A to I). The investigated and assessed properties (A to I) as well as the assessment criteria are summarized in Table 1 below. The results are given in Tables 2 and 3 below.

TABLE 1

Tests A to I as well as assessment criteria

| | Tests | Assessment criteria | |
|---|---|---|---|
| A | "Foam formation" | | |
| | The mixture was shaken vigorously in a bottle, the | – | strong |
| | bottle was left to stand for 2 minutes, and the foam | + | average |
| | formation in the bottle was visually assessed. | ++ | weak |
| | | +++ | no foam |
| B | "Film formation" | | |
| | The mixture was sprayed onto a rough film, and the | – | no film |
| | uniformity of the film with respect to edge sharpness | + | non-uniform |
| | and homogeneity was visually assessed. | ++ | semi-uniform |
| | | ++ | uniform |
| C | "Drop formation" | | |
| | After spraying the mixture onto a rough film, the | – | large drops |
| | formation and shape of droplets was visually | + | small drops |
| | assessed. | ++ | no drops |
| D | "Dwell time of film/bubbles" | | |
| | After spraying the mixture onto a rough film, the dwell time of the sprayed film or the formed bubbles was determined. | | in hours (h) |
| E | "Eyelet test" | | |
| | A (wire) eyelet (diameter 2 cm) was submerged in | – | <1 sec |
| | the mixture, lifted out, and the duration (shelf life) of | + | 2-5 sec |
| | the film in the eyelet was determined. The durability | ++ | >5 sec |
| | of the film in the eyelet provides information about the surface tension of the mixture. | + | >10 sec |
| F | "Gliding ability" | | |
| | The mixture was sprayed onto a rough film, and the | + | weak |
| | gliding ability was assessed by way of the behavior | ++ | average |
| | when rubbed with a PE film glove. | ++ | good |
| G | "Special" | | |
| | Specifics of the tests | | Description |
| | Monitoring of the mixtures in the bottle after 10 days | | |
| H | "Gel streaking" | | |
| | The mixture was left in a bottle for 10 days, and then | – | average |
| | the formation of debonded gel streaks at the bottom | + | weak |
| | of the bottle was assessed | ++ | absent |
| I | "Foam formation after 10 days" | | |
| | The mixture was left in a bottle for 10 days, and | – | strong |
| | foam formation was assessed as in test A. | + | weak |
| | | ++ | absent |

TABLE 2

| Single substances and combinations of two with Natrosol | | | | | | | | | | |
|---|---|---|---|---|---|---|---|---|---|---|
| No. (#) | Emulsifier Imwitor [wt. %] | Detergent Kolliphor [wt. %] | Gel forming-agent Natrosol [wt. %] | A Foam formation | B Film formation | C Drop formation | D Dwell time | E Eyelet test | F Gliding ability | G Special |
| 1 | 2.0 | | | +++ | + | ++ | 1 hr. | – | +++ | |
| 2 | | 2.0 | | ++ | + | + | 2-3 hrs. | + | ++ | |
| 3 | | | 0.2 | +++ | – | – | 3 hrs.+ | ++ | ++ | Beads |
| 4 | | | 0.4 | +++ | – | – | 3 hrs.+ | +++ | ++ | Beads |
| 5 | | | 0.6 | +++ | – | – | 3 hrs.+ | +++ | +++ | Beads |
| 6 | 1.0 | | 0.2 | +++ | + | ++ | 1 hr.+ | – | +++ | Cone 20° |
| 7 | | 1.0 | 0.2 | ++ | – | + | 2 hrs.+ | ++ | +++ | Beam |

TABLE 3

| Combinations of emulsifier, detergent, and gel-forming agent | | | | | | | | | | | | |
|---|---|---|---|---|---|---|---|---|---|---|---|---|
| No. (#) | Emulsifier Imwitor [wt. %] | Detergent Kolliphor [wt. %] | Gel forming-agent Natrosol [wt. %] | A Foam formation | B Film formation | C Drop formation | D Dwell time | E Eyelet test | F Gliding ability | G Special | H Gel streaking (10 days) | I Foam formation (10 days) |
| 8 | 1.0 | 1.0 | 0.4 | ++ | ++ | + | 2-3 hrs. | ++ | ++ | | – | ++ |
| 9 | 1.0 | 1.5 | 0.4 | + | + | ++ | 2-3 hrs. | + | +++ | | – | ++ |
| 10 | 1.0 | 2.0 | 0.4 | + | + | ++ | 2-3 hrs. | – | ++ | | – | ++ |
| 11 | 0.66 | 1.33 | 0.27 | – | + | + | 2-3 hrs. | ++ | + | Very much foam | ++ | + |
| 12 | 1.0 | 1.0 | 0.2 | – | + | ++ | 2-3 hrs. | – | +++ | Bottom streaking | – | ++ |
| 13 | 1.0 | 1.5 | 0.2 | – | + | ++ | 2-3 hrs. | ++ | +++ | | + | + |
| 14 | 1.0 | 2.0 | 0.2 | – | ++ | ++ | 2-3 hrs. | +++ | +++ | | ++ | + |
| 15 | 2.0 | 1.0 | 0.4 | ++ | + | + | 2-3 hrs. | – | ++ | | + | ++ |
| 16 | 2.0 | 1.5 | 0.4 | + | + | ++ | 2-3 hrs. | ++ | ++ | | ++ | ++ |
| 17 | 2.0 | 2.0 | 0.4 | + | ++ | + | 2-3 hrs. | +++ | ++ | | – | + |
| 18 | 1.3 | 3 | 0.3 | + | + | ++ | 2-3 hrs. | + | +++ | | + | ++ |
| 19 | 0.89 | 3.33 | 0.2 | + | +++ | – | 2-3 hrs. | + | +++ | Many bubbles | ++ | – |
| 20 | 2.0 | 1.0 | 0.2 | ++ | ++ | ++ | 2-3 hrs. | – | +++ | | ++ | ++ |
| 21 | 2.0 | 1.5 | 0.2 | + | + | (+) | 2-3 hrs. | ++ | ++ | Bottom streaking | – | ++ |
| 22 | 2.0 | 2.0 | 0.2 | + | + | ++ | 2-3 hrs. | (+) | +++ | Spray jet, no cone, bubbles | – | ++ |

Example 2

Among the compositions from Example 1, Table 3, promising mixtures were selected, further diluted, and tested "in vivo" on the patient's skin. The sonic transmission properties were equally good for all mixtures.

The selected compositions were investigated and assessed for different properties (J to N). A commercially available contact medium gel (Sonogel, Sonogel Vertriebs GmbH) was used as the comparative composition. The investigated and assessed properties (J to N) as well as the assessment criteria are summarized in Table 4 below, and the results are given in Table 5 below.

TABLE 4

| Tests J to I and assessment criteria | | | |
|---|---|---|---|
| | Tests on the skin | Assessment criteria | |
| J | Spray property "Spray cone" | | |
| | The mixture was sprayed with a simple spray head. The angle of the spray cone was estimated based on a template, or the occurrence of only one spray jet without cone formation was registered. | "##" | estimated angular degree of spray cone |
| | | 0 | Spray jet without cone |
| K | "Film formation - skin" | | |
| | After spraying the mixture onto the skin, the formation of a homogeneous film was assessed. | – | no |
| | | + | limited |
| | | +++ | yes |

TABLE 4-continued

Tests J to I and assessment criteria

| | Tests on the skin | | Assessment criteria |
|---|---|---|---|
| L | "Drop formation- skin" | | |
| | After spraying the mixture onto the skin, the | − | yes |
| | formation of drops was visually assessed. | +++ | no |
| M | "Gliding ability - skin" | | |
| | After spraying the mixture onto the skin, the gliding | + | limited |
| | ability of the probe head within the applied film was | ++ | moderate |
| | assessed. | +++ | good |
| N | "Gliding ability - distance" | | |
| | The distance beyond which the probe head glides | − | <<3 cm (poor) |
| | outside of the circumscribed liquid film on the liquid | + | >3 cm |
| | film was determined as part of the gliding ability of | ++ | >4 cm |
| | the probe head (M). | + | >5 cm |

Example 3

Based on the composition #28 (0.5% Imwitor, 0.125% Kolliphor, 0.2% Natrosol) from Example 2, Table 5, various dilutions were prepared by adding water (#28/water: 2/1=66%; 1/1=50%; 1/2=33%). The spraying behavior was assessed as compared to the undiluted composition (I/O=100%). The pH level of the compositions was 5.9. No foam formation was observed in any of the compositions after the previous test A.

In a further step, the dilutions and undiluted composition were mixed with preservatives (0.4 wt. % sodium benzoate+ 0.15 wt. % potassium sorbate) and different concentrations of citric acid were added, and the pH level was determined again. The addition of preservative did not change the starting pH level of the compositions. The results are given in Table 6 below.

Example 4

The composition #28 (0.5% Imwitor, 0.125% Kolliphor, 0.2% Natrosol) and its dilutions from Example 3 were assessed for spray properties, film formation, and gliding ability according to the previous tests J, K, M, and N according to Example 2. In addition, substance losses were assessed by drying in that 0.8 mL of the composition was spread over a surface area of 20 cm 2 skin and the surface loss was determined after 1 hour at ambient temperature. The results are given in Table 7 below.

Example 5

The specific gravity was determined from compositions #10, 14, 17, 23, 28 and the flowability was measured at 25 °C and at 37 °C in accordance with DIN EN ISO 2431: 2020-02. The results are given in Table 8 below.

TABLE 5

Selected mixtures and their dilutions

| No. (#) | Emulsifier Imwitor [wt. %] | Detergent Kolliphor [wt. %] | Gel forming-agent Natrosol [wt. %] | J Spray cone [°] | K Film formation (skin) | L Drop formation (skin) | M Gliding ability (skin) | N Gliding ability (distance) | Preference | pH level |
|---|---|---|---|---|---|---|---|---|---|---|
| 23 | 1 | 0.25 | 0.2 | 20 | +++ | +++ | +++ | +++ | X | 5.6 |
| 24 | 1 | 0.1 | 0.4 | 0 | − | − | + | ++ | | 5.6 |
| 25 | 1 | 0.1 | 0.3 | 20 | + | +++ | ++ | + | | 5.9 |
| 26 | 0.9 | 0.45 | 0.18 | 30 | +++ | +++ | + | + | | 5.9 |
| 27 | 0.5 | 0.125 | 0.4 | 0 | +++ | +++ | + | + | | 5.9 |
| 28 | 0.5 | 0.125 | 0.2 | 30 | +++ | +++ | +++ | +++ | X | 5.9 |
| 29 | 0.1 | | 0.2 | 0 | − | − | ++ | + | | 5.9 |
| 30 | | | 0.3 | 0 | − | − | + | − | | 6.8 |
| Cf. | | Sonogel | | not applicable | not applicable | not applicable | ++ | ++ | | |

TABLE 6

Spray behavior of different dilutions of the composition #28

| No. (#) | Dilution #28/$H_2O$ | Emulsifier Imwitor [wt. %] | Detergent Kolliphor [wt. %] | Gel forming-agent Natrosol [wt. %] | J Spray cone [°] | pH level before/after addition of citric acid [wt. %] 0% | 0.5% | 1.0% | 1.5% | 2.0% |
|---|---|---|---|---|---|---|---|---|---|---|
| 28 | 1/0 (100%) | 0.5 | 0.125 | 0.2 | 30 | 5.9 | 5.9 | 5.6-5.9 | 5.6-5.9 | 5.6 |
| 28a | 2/1 (66%) | 0.375 | 0.0932 | 0.15 | 20 | 5.9 | 5.9 | 5.9 | 5.9 | 5.6 |

TABLE 6-continued

Spray behavior of different dilutions of the composition #28

| No. | Dilution | Emulsifier Imwitor | Detergent Kolliphor | Gel forming-agent Natrosol | J Spray cone | pH level before/after addition of citric acid [wt. %] | | | | |
|---|---|---|---|---|---|---|---|---|---|---|
| (#) | #28/$H_2O$ | [wt. %] | [wt. %] | [wt. %] | [°] | 0% | 0.5% | 1.0% | 1.5% | 2.0% |
| 28b | 1/1 (50%) | 0.25 | 0.0625 | 0.1 | 40 | 5.9 | 5.9 | 5.9 | 5.9 | 5.6 |
| 28c | 1/2 (33%) | 0.166 | 0.0412 | 0.066 | 70 | 5.9 | 5.9 | 5.9 | 5.6 | 5.6 |

TABLE 7

Spray behavior. film formation, gliding ability, and surface loss of various dilutions of the composition #28

| No. (#) | Dilution #28/$H_2O$ | Emulsifier Imwitor [wt. %] | Detergent Kolliphor [wt. %] | Gel forming-agent Natrosol [wt. %] | J Spray cone [°] | K Film formation (skin) | M Gliding ability (skin) | N Gliding ability (distance) | Drying Surface loss |
|---|---|---|---|---|---|---|---|---|---|
| 28 | 1/0 (100%) | 0.5 | 0.125 | 0.2 | 30 | +++ | +++ | +++ | 10% |
| 28a | 2/1 (66%) | 0.375 | 0.0932 | 0.15 | 20 | +++ | +++ | +++ | 20% |
| 28b | 1/1 (50%) | 0.25 | 0.0625 | 0.1 | 40 | +++ | +++ | +++ | 5% |
| 28c | 1/2 (33%) | 0.166 | 0.0412 | 0.66 | 70 | +++ | + | + | 0 |

TABLE 8

Flowability (ISO 2431) of the compositions #10, 14, 17, 23, 28 at 25° C. and 37° C.

| No. (#) | Emulsifier Imwitor [wt. %] | Detergent Kolliphor [wt. %] | Gel forming-agent Natrosol [wt. %] | Spec. gravity [g/ml] | 25° C. Efflux time [sec] | 37° C. Efflux time [sec] |
|---|---|---|---|---|---|---|
| 10 | 1.0 | 2.0 | 0.4 | 1.03 | 18 | 16 |
| 14 | 1.0 | 2.0 | 0.25 | 1.02 | 13 | 13 |
| 17 | 2.0 | 2.0 | 0.4 | 1.01 | 24 | 21 |
| 23 | 1.0 | 0.25 | 0.2 | 1.00 | 14 | 13 |
| 28 | 0.5 | 0.125 | 0.2 | 1.00 | 13 | 13 |
| 28x | 0.5 | 0.125 | 0.2 | 0.97 | 10 | 10 |

Sample # 28x also contains preservatives (0.4 wt. % sodium benzoate + 0.15 wt. % potassium sorbate) compared to sample # 28 and was adjusted to pH level = 5.6 with citric acid.

Discussion of Results

Pure water is highly fluid and therefore also very well sprayable, and it also does not form gas bubbles. However, compared to the contact medium compositions according to the invention, which are also very well sprayable and exhibit no or only marginal gas bubble formation, water beads off the skin without forming a liquid film Water alone is therefore unusable as a contact medium.

Only the combination of gel-forming agent, detergent, and emulsifier according to the invention provided excellent properties, in particular good gliding properties, good film formation, low to no foam formation, and very good sound transmission properties.

In quantitative terms, in particular, the combination of gel-forming agent, detergent, and emulsifier produced surprisingly good results. As expected, higher concentrations demonstrated the good properties of the mixture, oriented towards the criteria described. It was surprising that these properties were also observed even at low concentrations.

A further advantage of the invention was sprayability of the contact medium according to the invention compared to conventional contact medium gels. Moreover, the contact medium can also be heated up to body temperature without a loss of function. For this purpose, heating apparatuses are suitable, for example, for keeping infant milk bottles warm in use. Other apparatuses, such as heating pads, are conceivable. In the medical field, the medium can be used in both diagnostic and therapeutic ultrasonics, regardless of the different types of transducers and ultrasonic techniques. In addition to the application in medical ultrasonics, the contact medium according to the invention can also advantageously be used in electrocardiography (ECG), in defibrillation, and outside the medical field (e.g., technical ultrasonics).

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A contact medium comprising:

0.05 to 0.5 wt. % of a gel-forming agent;

0.05 to 3.5 wt. % of a detergent;

0.1 to 4.0 wt. % of an emulsifier;

optionally additives, preferably selected from a preservative, an acidifier, a skincare additive, and mixtures thereof, and wherein a balance of the contact medium comprises water, wherein the gel-forming agent is selected from a group consisting of: hydroxyethyl cellulose, carboxycellulose, xanthan gum, guar gum, collagen, gelatin, pectins, chitin, starch, alginates, including sodium alginate, potassium alginate, calcium alginate, and mixtures thereof, wherein the detergent is a non-ionic surfactant or a mixture of non-ionic surfactants, wherein the emulsifier is selected from a group consisting of: glycerol mono fatty acid esters, glycerol di-fatty acid esters, and mixtures thereof, wherein any remaining fatty acid is derived from C7-C20-saturated fatty acid, C16-C20-monounsaturated fatty acid, C18-C20-diunsaturated fatty acid, or a combination thereof, and wherein the contact medium has a pH value in a range of 5 to 7 and wherein the contact medium has an efflux time determined in accordance with DIN EN ISO 2431:2020-02 using an efflux beaker with a 4 mm nozzle at 25 °C, in a range of 5 to 200 seconds.

2. The contact medium according to claim 1, wherein >80 wt. % is hydroxyethyl cellulose having an average degree of substitution (DS) of 0.85-1.35, or a molar degree of substitution of 1.5-3.0, or both.

3. The contact medium according to claim 1, wherein >80 wt. % of the detergent is polyethoxylated castor oil.

4. The contact medium according to claim 1, wherein the detergent is selected from a group consisting of: polyethoxylated castor oil, poloxamers, and mixtures thereof.

5. The contact medium according to claim 1, wherein >80 wt. % of the emulsifier is glycerol mono-fatty acid ester.

6. The contact medium according to claim 1, wherein the pH value is in a range of 5 to 6.5.

7. The contact medium according to claim 1, further comprising the preservative, and wherein the preservative is selected from a group consisting of: sodium benzoate, potassium benzoate, sodium sorbate, potassium sorbate, and mixtures thereof.

8. The contact medium according to claim 1, further comprising the skincare additive.

9. The contact medium according to claim 1, wherein the contact medium comprises at most 1 wt. % of a monovalent alkanol.

10. The contact medium according to claim 1, further comprising: 0.1 to 0.3 wt. % of the gel-forming agent, or 0.075 to 0.5 wt. % of the detergent, or 0.2 to 0.8 wt. % of the emulsifier, or any combination thereof.

11. A kit comprising:

a contact medium according to claim 1, and at least one applicator.

12. The kit according to claim 11, further comprising: at least one heating apparatus configured to heat the contact medium.

13. The kit according to claim 11 further comprising: at least one refilling container filled with contact medium.

14. The contact medium of claim 6, further comprising an inorganic or organic buffer system or acidifier for adjusting the pH level.

15. The contact medium of claim 6, wherein the inorganic or organic buffer system or acidifier is selected from a group consisting of: citric acid, sodium citrate-citric acid buffer, and phosphate-citrate buffer.

16. The contact medium of claim 6, comprising the preservative in a quantity from 0.05 to 1.0 wt. %.

* * * * *